United States Patent
Favero et al.

(10) Patent No.: US 10,422,731 B2
(45) Date of Patent: Sep. 24, 2019

(54) DEVICE FOR IN-LINE MONITORING OF THE QUALITY OF A WATER-SOLUBLE POLYMER SOLUTION MANUFACTURED FROM INVERT EMULSION OR POWDER OF SAID POLYMER

(71) Applicant: S.P.C.M. SA, Andrezieux Boutheon (FR)

(72) Inventors: Cedrick Favero, Saint Romain le Puy (FR); Christophe Rivas, Saint Romain le Puy (FR)

(73) Assignee: S.P.C.M. SA (FR)

( * ) Notice: Subject to any disclaimer, the term of this patent is extended or adjusted under 35 U.S.C. 154(b) by 241 days.

(21) Appl. No.: 15/557,417

(22) PCT Filed: Mar. 9, 2016

(86) PCT No.: PCT/FR2016/050534
§ 371 (c)(1),
(2) Date: Sep. 11, 2017

(87) PCT Pub. No.: WO2016/142623
PCT Pub. Date: Sep. 15, 2016

(65) Prior Publication Data
US 2018/0275037 A1    Sep. 27, 2018

(30) Foreign Application Priority Data

Mar. 11, 2015    (FR) ...................................... 15 52037

(51) Int. Cl.
*G01N 11/08* (2006.01)
*G01N 13/00* (2006.01)
(Continued)

(52) U.S. Cl.
CPC ............ *G01N 11/08* (2013.01); *E21B 21/062* (2013.01); *E21B 43/16* (2013.01); *E21B 43/20* (2013.01);
(Continued)

(58) Field of Classification Search
CPC ...... G01N 1/2035; G01N 11/08; G01N 13/00; G01N 2001/2064; G01N 2011/0046;
(Continued)

(56) References Cited

U.S. PATENT DOCUMENTS 3,924,448 A * 12/1975 Howard ................. G01N 11/08
73/54.04
4,395,340 A * 7/1983 McLaughlin ............. C08F 2/10
166/266
(Continued)

FOREIGN PATENT DOCUMENTS

| EP | 1437173 A1 | 7/2004 |
| WO | 2011076863 A1 | 6/2011 |
| WO | 2012140092 A1 | 10/2012 |

*Primary Examiner* — David J Bolduc
(74) *Attorney, Agent, or Firm* — Forge IP, PLLC

(57) ABSTRACT

An apparatus for monitoring the effective dissolving of a polymer when the use region is not accessible. The apparatus includes a pipe on which are inserted, consecutively: a pump, a flowmeter, a water or brine inlet mechanism for diluting the mother solution flowing in the pipe, a mixer capable of in-line homogenization of the diluted mother solution, a first tube calibrated to simulate the distance and the conditions for moving the diluted solution in the main pipe between the point where the mother solution is diluted and the use region, a mechanism capable of reducing the pressure of the diluted solution flowing in the pipe upstream of the first tube that is calibrated from 10 to 10000 kPa (from 0.1 to 100 bar), a second calibrated tube for creating a head (Continued)

loss, and a device for measuring differential pressure between the inlet and the outlet of the second calibrated tube.

13 Claims, 1 Drawing Sheet

(51) Int. Cl.
*E21B 43/20* (2006.01)
*E21B 21/06* (2006.01)
*E21B 43/16* (2006.01)
*E21B 47/00* (2012.01)
*G01N 1/20* (2006.01)
*G01N 11/00* (2006.01)

(52) U.S. Cl.
CPC .......... *E21B 47/00* (2013.01); *E21B 47/0001* (2013.01); *G01N 1/2035* (2013.01); *G01N 13/00* (2013.01); *G01N 2001/2064* (2013.01); *G01N 2011/0046* (2013.01); *G01N 2013/006* (2013.01)

(58) Field of Classification Search
CPC . G01N 2013/006; E21B 21/062; E21B 43/16; E21B 43/20; E21B 47/00; E21B 47/001
See application file for complete search history.

(56) References Cited

U.S. PATENT DOCUMENTS

| | | | |
|---|---|---|---|
| 4,627,271 A * | 12/1986 | Abbott | G01N 11/08 73/54.06 |
| 4,821,564 A | 4/1989 | Pearson et al. | |
| 4,845,981 A | 7/1989 | Pearson | |
| 5,283,001 A * | 2/1994 | Gregoli | B01F 3/0807 137/13 |
| 5,426,137 A * | 6/1995 | Allen | B01F 3/1271 366/158.4 |
| 2006/0225924 A1* | 10/2006 | Ivan | B01F 3/1271 175/66 |
| 2008/0264641 A1* | 10/2008 | Slabaugh | B01F 3/0861 166/308.2 |
| 2009/0090504 A1 | 4/2009 | Weightman et al. | |
| 2009/0242201 A1* | 10/2009 | Van Beurden | E21B 21/062 166/275 |
| 2010/0254214 A1* | 10/2010 | Fisher | B01F 3/1214 366/152.2 |
| 2011/0297399 A1* | 12/2011 | Dyck | E21B 21/106 166/386 |
| 2012/0199356 A1* | 8/2012 | Nichols | B01F 3/1221 166/308.1 |
| 2013/0024132 A1 | 1/2013 | Caspar et al. | |
| 2013/0098611 A1* | 4/2013 | Salgaonkar | C09K 8/00 166/278 |
| 2014/0053637 A1 | 2/2014 | Quillien et al. | |
| 2014/0202702 A1* | 7/2014 | Cobb | B01F 5/0614 166/307 |
| 2015/0204165 A1* | 7/2015 | Yeung | E21B 21/062 166/244.1 |
| 2015/0218440 A1* | 8/2015 | Johnson | E21B 43/26 166/308.1 |
| 2016/0024367 A1* | 1/2016 | Zha | C09K 8/64 166/308.2 |
| 2016/0168954 A1* | 6/2016 | Pich | E21B 43/16 166/250.01 |
| 2017/0274333 A1* | 9/2017 | Smith | B01F 5/102 |

* cited by examiner

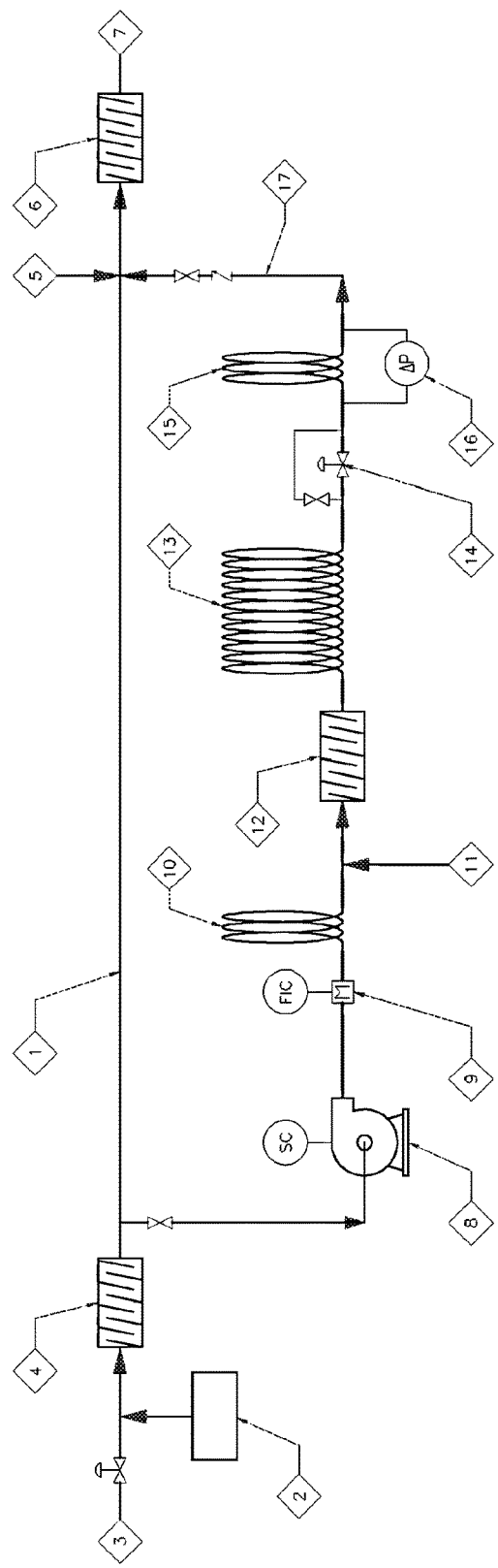

DEVICE FOR IN-LINE MONITORING OF THE QUALITY OF A WATER-SOLUBLE POLYMER SOLUTION MANUFACTURED FROM INVERT EMULSION OR POWDER OF SAID POLYMER

FIELD OF INVENTION

The invention relates to an apparatus for monitoring the effective dissolving of a polymer when the use region is not accessible.

BACKGROUND OF THE INVENTION

Water-soluble polymer invert emulsions (water-in-oil) are widely used in many domains for the thickening and flocculating properties thereof. This particular form has the advantage of being able to provide, in concentrated liquid form, high molecular weight polymers. The emulsion, however, should ideally be inverted in more or less concentrated form prior to the use of the polymer, mixing water with the invert emulsion in such a way as to obtain a continuous aqueous phase wherein the polymer is located.

The invert emulsions, dehydrated or not, of acrylamide-based water-soluble polymers are useful in particular in enhanced oil recovery (RAP or EOR for Enhanced Oil Recovery) and more particularly in off-shore operations. An aqueous polymeric solution is typically prepared on the platform. Generally, the emulsion is inverted by means of the addition of water and then mixed within a mixer, for example a static mixer, in order to produce a mother solution with a concentration of between 2,000 and 20,000 ppm. The mother solution itself is diluted downstream with water or brine in order to produce the polymeric solution injected into the subterranean formation, wherein the polymer concentration is typically in the range of 100 to 2,500 ppm.

It is essential that the emulsion be well inverted because in being well inverted it will provide the polymer solution with optimum viscosity and injectivity, the polymer being completely available and homogeneously distributed in order to thicken the aqueous medium. When the emulsion is not properly inverted part of the polymer does not perform the thickening role thereof, resulting in a loss of efficiency and injectivity of the solution prepared from the emulsion.

Likewise, water-soluble polymers in powder form are particularly useful in enhanced oil recovery especially in on-shore operations. The powders are prepared in the form of a solution by means of the dissolving of the powder in a more or less concentrated solution. Generally, the powder is dissolved by virtue of a dissolving apparatus, such as the PSU (Polymer Slicing Unit) described in WO2011/1076863, to a mother solution concentration ranging between 2,000 and 20,000 ppm, said mother solution being deposited in maturing tanks under agitation, then diluted downstream with water to produce said diluted polymeric solution wherein the polymer concentration is typically of the order of 100-2500 ppm.

It is also essential that the powder be well dissolved and the polymer well solubilized in water or brine.

Subsequently, the expression "effective polymer solution preparation" denotes the implementation thereof under conditions that make it possible to obtain optimum solution viscosity. The optimum solution viscosity is the viscosity attained when 100% of the water-soluble polymer is dissolved in water or brine. This optimum viscosity is in practice between 1 and 200 mPa·s (between 1 and 200 cps) (measured at 20° C. using a Brookfield rheometer with a UL module).

The term 'use region', refers to the most downstream location theoretically accessible to the method wherein the polymeric aqueous solution is used. For example, in the case of an EOR Off-shore operation, this location is at the swivel in the subterranean formation located at the bottom of the sea or ocean.

For this, it is known to occasionally take a sample of the polymeric aqueous solution in order to verify the viscosity thereof in relation to the viscosity of a solution prepared under optimal laboratory conditions.

However, in the case where the diluted solution is not accessible or not easily accessible, it is sometimes impossible to collect a sample of the solution. This is typically the case at the wellhead when it is at the bottom of the sea or ocean in an off-shore operation, wherein the difficulty is technical. This is also the case when the mother solution is for example prepared within a centralized dissolving station and then transported through long pipelines to dilution sub-stations and finally to the injection wells. The wellhead can then be located within a risk zone (military zone) or within a restricted access protected area in an onshore operation, where the solution preparation location is situated within an accessible area. The problem may arise in many other cases.

SUMMARY OF THE INVENTION

The problem that the invention proposes to solve is the provision of an apparatus for monitoring the effective dissolving (emulsion inversion or powder solubilizing) of a water-soluble polymer within a diluted solution in the case where the diluted solution cannot be removed, i.e. when it is not accessible or not easily accessible.

The applicant has developed an apparatus that makes it possible to achieve these objectives.

In a first aspect, the invention relates to a device destined to be connected in shunt between 2 points of a main pipe, respectively:
- a first point whereupon a water-soluble polymer mother solution is formed, obtained by means of mixing water or brine with an invert emulsion of said polymer, that is possibly dehydrated or a powder of said polymer,
- and a second point near to where the mother solution is diluted.

The device of the invention makes it possible to monitor the effective dissolving of the mother solution after dilution, between the point of introduction of the mother solution into the main pipe and the use region thereof, particularly in cases where the diluted solution is not accessible or not easily accessible.

It includes a pipe on which are inserted, consecutively:
- a pump,
- a flowmeter,
- a water or brine inlet means for diluting the mother solution flowing in the pipe,
- a mixer capable of in-line homogenization of the diluted mother solution,
- a first tube that is calibrated so as to simulate the distance and the conditions for moving the diluted solution in the main pipe between the point where the mother solution is diluted and the use region, a means that is capable of reducing the pressure of the diluted solution flowing in the pipe upstream of the first tube that is calibrated from 10 to 10000 kPa (from 0.1 to 100 bar), a second calibrated tube for creating a head loss, a device for measuring differential pressure between the inlet and the outlet of the second calibrated tube.

This apparatus makes it possible to reliably monitor, by virtue of the measurement of the viscosity of the solution, the satisfactory or unsatisfactory inversion of an invert emulsion or the satisfactory or unsatisfactory solubilization of a powder of water-soluble polymers within facilities wherein sampling cannot take place because the area of application of the polymer is not accessible or not easily accessible.

In a second aspect, the invention concerns a method for monitoring the effective dissolving of a water-soluble polymer at the use region thereof, in cases where the solution is not accessible or not easily accessible.

The water-soluble polymers are natural, semisynthetic or synthetic polymers. Synthetic polymers that are based upon acrylamide are preferred.

The powder polymers are obtained by means of a gel process. The polymers in emulsion are obtained by means of emulsion polymerization, so-called invert, optionally followed by a dehydration step.

The pump may be of different, preferably volumetric, types. The pump may also be centrifugal in the case of low pressures (less than 10000 kPa (100 bar)). The flow rate thereof is typically between 0.001 and 0.1 m$^3$/h (from 1 L/h to 100 L/h).

The flowmeter can be of any type. This is preferably a precision flowmeter of the Coriolis effect mass flow type, or of an electromagnetic type.

In order to dilute the solution the water or brine inlet means is typically in the form of a pipe or tube carrying the water or brine, said pipe being connected to the pipe of the apparatus. As already mentioned, a pump and a flow meter are positioned upstream of this inlet in such a way as to push the water or brine into the shunt at the necessary pressure and flow rate.

The mixer allows for the homogenization of the mother solution with the previously added water or brine. This requires a carefully designed mixer ensuring the mixing of the solution and limiting the mechanical degradation of the polymer, which is highly sensitive to shearing.

For example a dynamic mixer can be used consisting of a low shear rotor making it possible to incorporate the mother solution into the brine. In an advantageous embodiment, the mixer is a static mixer of the type marketed by the companies Sulzer Chemtech 25 Ltd.—Sulzer—Allee 48—CH 8404 Winterthur—Switzerland for Europe, and Kenics, Chemineer Inc, 125 Flagship Drive, North Andover, Mass. 01845 USA. The static mixer is preferably of a type such as those described in the document EP1437173, and marketed by SULZER under the names SMX and SMV.

Advantageously, the static mixer comprises at least a unitary mixing element having a lattice structure. Each mixing element comprises an external cylindrical body containing the actual mixing elements, which are in the form of a specific lattice structure. The diameters of the mixing elements are variable and adjustable as a function of the head loss that they generate. The static mixer preferably produces a head loss of between 100 and 500 kPa (between 1 and 5 bar), preferably between 200 and 300 kPa (between 2 and 3 bar).

The static mixer advantageously comprises 10 to 50 mixing elements, more advantageously 20 to 30 mixing elements.

The first tube is calibrated in such a way as to make it possible to simulate the distance and the conditions (shear, Reynolds number, residence time, diameter, etc.) for moving the diluted solution in the main pipe between the point where the mother solution is diluted and the use region, The dimensions thereof (length, internal diameter) and the nature thereof are determined as a function of the means that make it possible to deliver the diluted solution from the dilution zone to the use region. Preferably, in order to reduce the size thereof, said tube has the form of a coil.

The means capable of reducing the pressure from 10 to 10,000 kPa (from 0.1 to 100 bars) is typically in the form of a valve called a "choke" in the field of enhanced oil recovery. The valve makes it possible to adjust the pressure at which the diluted solution is used. For example, in the EOR process, this makes it possible to monitor the injection pressure of the polymeric solution within the subterranean formation The second calibrated tube makes it possible to create a head loss wherein the amplitude is measured by virtue of apparatus for measuring the differential pressure between the inlet and the outlet of the second tube. Preferably, in order to reduce the size thereof, said tube has the form of a coil.

In a preferred embodiment, said second calibrated tube measures between 10 and 30 meters long, with an internal diameter of 5 to 20 mm, the wall having a thickness of 2 to 5 mm. The dimensions thereof can be modified, by a person skilled in the art, such as to arrive at the condition that allows for a sufficient drop in pressure for the apparatus to be able to measure the differential pressure.

The differential pressure measurement device makes it possible to measure the head loss within the second calibrated tube, said head loss being less than 200 kPa (2 bars). Generally, the head loss produced by the calibrated tube is between 1 and 200 kPa (between 0.01 and 2 bars). As already indicated, a person skilled in the art will be able to adapt the dimensions of the calibrated tube as a function of the head loss. A device of this type is for example described in the document WO2012/140092.

The apparatus can further comprise:

a third calibrated tube in order to simulate the distance and the conditions for moving the mother solution in the main pipe between the point where the solution is produced and the point where it is diluted, the tube being located preferably between the flowmeter and the water or brine inlet means. In practice, the tube is in the form of a coil.

an apparatus for the in-line measurement of the concentration of the water-soluble polymer. It can for example be an apparatus measuring the conductivity of the polymeric solution, thereby making it possible to deduce the concentration of the polymer within the solution, as described within the document EP 2 734 475. Said apparatus is preferably positioned between the flowmeter and the water or brine inlet means. Said apparatus is particularly dedicated to the measurement of the polymeric concentration of a solution called "mother" and comprising of between 2000 and 2000 ppm of polymer in a salt water matrix.

a single or double filter with a lattice of 5 to 20 microns, making it possible to eliminate those materials in suspension that can block the pump or the flowmeter. Said filter is advantageously positioned before the pump.

a pulsation absorber is advantageously positioned before the pump.

Within the apparatus according to the invention, the pump, the tubes and the flowmeter are able to withstand pressures of 40,000 kPa (of 400 bars), They are advantageously manufactured in a material chosen from the group comprising:

austenitic-ferritic steels, advantageously the austenitic-ferritic steels containing between 24 and 26% chromium and between 6 and 8% nickel;

superalloys containing mainly nickel, but also several metals such as chromium, magnesium, iron and titanium (Hastelloy).

These materials make it possible to deal with all compositions encountered for the preparation of polymeric solutions, including the brines used in EOR processes.

The apparatus according to the invention is especially intended to be used at pressures ranging from 5000 to 40,000 kPa (from 50 to 400 bar).

Located upstream of the first point of the main pipe there is typically equipment that makes it possible to combine either the invert emulsion or the water-soluble polymer powder with water or a brine. In the case of an invert emulsion, the equipment is typically a mixer, preferably a static mixer of the same type as present within the apparatus according to the invention. This is the case for example in an EOR off-shore process. In the case of a powder, the equipment is typically dissolving equipment such as the PSU (Polymer Slicing Unit) described within the document WO20111076863. This is the case for example in an EOR off-shore process.

Downstream of the second point of the main pipe there is typically a means for combining the mother solution obtained by means of the inversion of the invert emulsion or by means of the dissolving of the water-soluble polymer powder with water or a brine, for example a static mixer, the diluted solution being then transported to the use region which may be located several kilometers away from the dilution site.

According to the invention, the head loss, continuously measured under high pressure within the second calibrated tube producing the head loss, is extrapolated at the corresponding viscosity of the water-soluble polymer solution, measured at atmospheric pressure within a Brookfield apparatus under the same conditions of concentration, temperature and salinity but on an ad hoc basis. The viscosity of the solution is extrapolated as Viscosity Yield, i.e. with low shear.

In order to obtain good correlations, it is important that the shear rates in the second calibrated tube be low and similar to those observed with a Brookfield viscometer, an apparatus that is widely used in the water-soluble polymers industry, as well as in the application of enhanced oil recovery.

More specifically, the shear rate in the second calibrated tube is preferentially between $1\ s^{-1}$ and $500\ s^{-1}$, and very preferentially between $5\ s^{-1}$ and $200\ s^{-1}$.

The shear rates are therefore considered to be weak and this is made possible by virtue of the low velocity of the fluid within the second calibrated tube, and this under high pressure.

The viscosities deriving from the pressure difference will range from 0.5 to 1000 mPa·s (0.5 to 1000 cps), preferably from 1 to 100 mPa·s (1 to 100 cps).

The satisfactory inversion of an invert emulsion or the satisfactory solubilization of a water-soluble polymer powder is then evaluated by a virtue of the ratio between the value of viscosity of the diluted solution, extrapolated from the head loss, and the viscosity of a solution from the same emulsion or from the same powder, wherein a solution is prepared at the same concentration under optimal laboratory conditions. The closer the ratio is to 1, the better the quality of the inversion or solubilization of the powder.

When this ratio is less than 0.9 or 0.8, or even 0.7, it can be concluded that the polymeric solution is not optimal, or as required in the use region. It is then necessary to check the various preparation and transportation parameters in order to identify the causes of this loss of efficiency. Once the problems have been resolved, the ratio will theoretically increase to a value close to 1.

The apparatus is particularly advantageous in an enhanced oil and/or off-shore gas recovery process. In this case, a water-soluble polymer invert emulsion is generally used. The apparatus is also perfectly suitable for an enhanced oil and/or on-shore gas recovery process. In this case, a water-soluble polymer powder is generally used.

The invention also relates to a method for monitoring the effective dissolving of a water-soluble polymer at the use region thereof where it is not accessible or not easily accessible, wherein, within a pipe:

a solution is formed, obtained by means of mixing water or brine with an invert emulsion of said polymer, that is possibly dehydrated or a power of said polymer, the mother solution is diluted, the diluted solution is transported to the use region thereof, between the formation of the mother solution and the dilution thereof, part of the stream flowing in the pipe is shunted in order to circulate it in the apparatus described above, the viscosity of the diluted solution is calculated by means of the extrapolation of the pressure difference measured by the differential pressure measuring device of the apparatus, the viscosity is measured of a polymer solution prepared at the same concentration as that of the diluted solution, and under optimum laboratory conditions.

the ratio is calculated between the value of viscosity obtained by extrapolation and the viscosity of the solution made in the laboratory, the satisfactory or unsatisfactory dissolving of the polymer is deduced therefrom.

In practice, the water-soluble polymer mother solution has a polymer concentration of between 2,000 and 20,000 ppm and the diluted solution has a polymer concentration of between 100 and 2,500 ppm.

The invention and advantages thereof will become more apparent from the FIGURE and from the following examples given in order to illustrate the invention and in a non-limiting manner.

BRIEF DESCRIPTION OF THE DRAWINGS

FIG. 1 shows an apparatus according to the present invention in particular comprising a shunt, installed on an injection pipe of a solution containing a water-soluble polymer in an enhanced oil recovery plant.

DETAILED DESCRIPTION OF THE INVENTION

The apparatus according to the present invention in particular comprises on the main pipe (1) a water-soluble polymer invert emulsion inlet (2), a water or brine inlet (3), a static mixer (4) allowing for the mixing of the two fluids into a solution called "mother", a second water or brine inlet (5) allowing for the dilution of this mother solution into a diluted solution, another static mixer (6) and means for transporting the mixture (7) to the use region which may be located several kilometers away from the dilution site, and bypassing the main line:

A volumetric pump (8) with a flow of 0.02 m$^3$/h (20 L/h);
A precision Coriolis effect flow meter (9);
A calibrated tube (10) to simulate the maturation of the polymer and the transportation of the mother solution to the point of dilution within the main pipe, said tube having a length of 50 meters, an internal diameter of 10 mm and being manufactured in super duplex steel;
a water or brine inlet (11) in order to dilute the mother solution;
a static mixer (12) allowing for the mixing of the mother solution and the water or brine;
A calibrated tube (13) to simulate the distance between the point of dilution and the use region, said tube having a length of 400 meters, an internal diameter of 20 mm and being manufactured in super duplex steel;
A valve (14) allowing for a pressure reduction of 500 kPa (5 bar);
A calibrated tube (15) creating a head loss of 10 to 200 kPa (from 0.1 to 2 bar)
A differential pressure measuring apparatus (16),
A conduit (17) for reinjecting the solution into the main pipe.

A copolymer of acrylamide and sodium acrylate (70/30 mol %) emulsion is implemented with a brine containing 3000 ppm of NaCl in an off-shore EOR process. The apparatus described above is used and positioned within the bypass of the main pipe. The pressure is 22,000 kPa (220 bar). The main pipe injection flow rate is 125 m$^3$/h. The polymer concentration of the mother solution is 10,000 ppm. The bypass flow rate is 0.005 m$^3$/h (5 L/s). The polymer concentration of the diluted solution is 500 ppm.

In a first test, an insufficient pressure difference of 150 kPa (1.5 bar) is intentionally created within the static mixer (6) comprising only two elements. The emulsion is implemented within the apparatus described above. The deduced and calculated viscosity is 15 mPa·s (15 cps). A 1000 ppm solution is made in the laboratory and the viscosity is measured at 27 mPa·s (27 cps). The ratio of these two viscosities is 0.56. This ratio is low, far from 1 and it can be inferred that the emulsion has not been properly inverted. The reason is of course insufficient mixing within the static mixer (6) resulting in poor inversion of the emulsion, which the apparatus makes it possible to detect, and that cannot be compensated for, neither by dilution nor the periods of maturation.

In a second test, the same emulsion is implemented in the same manner but the static mixer (6) creates a pressure differential of 1000 kPa (10 bar) by virtue of 8 elements. The emulsion is implemented within the apparatus described above. The deduced and calculated viscosity is 29 mPa·s (29 cps). A 500 ppm solution is made in the laboratory and the viscosity is measured at 32 mPa·s (32 cps). The ratio of these two viscosities is 0.91. This is good and makes it possible to conclude that inversion has taken place.

The invention claimed is:

1. An apparatus adapted to be connected in shunt between 2 points of a main pipe, respectively:
a first point whereupon a water-soluble polymer mother solution is formed, obtained by way of mixing water or brine with an invert emulsion of said polymer, or a powder of said polymer,
and a second point near to where the solution is diluted;
wherein the apparatus makes it possible to monitor the effective dissolving of the mother solution after dilution, between the point of introduction of the mother solution into the main pipe and the use region thereof;
the apparatus containing a pipe within which is inserted, consecutively:
a pump,
a flowmeter,
a water or brine inlet for diluting the mother solution flowing in the pipe,
a mixer adapted for in-line homogenization of the diluted mother solution,
a first tube that is calibrated so as to simulate a distance and conditions for moving the diluted solution in the main pipe between the point where the mother solution is diluted and a use region,
a means for reducing the pressure of the diluted solution flowing in the pipe upstream of the first tube that is calibrated from 10 to 10000 kPa (from 0.1 to 100 bar),
a second calibrated tube for creating a head loss,
a device for measuring differential pressure between the inlet and the outlet of the second calibrated tube.

2. The apparatus according to claim 1, wherein the flowmeter is a precision flowmeter of the Coriolis effect mass flow type, or of the electromagnetic type.

3. The apparatus according to claim 1, wherein the mixer is a static mixer.

4. The apparatus according to claim 1, wherein the second tube measures between 10 and 30 meters long with an internal diameter of 5 to 20 mm, the wall having a thickness of 2 to 5 mm.

5. The apparatus according to claim 1, comprising a third calibrated tube, in the form of a calibrated coil in order to simulate the distance and the conditions for moving the mother solution in the main pipe between the point where the solution is produced and the point where it is diluted, the tube being located between the flowmeter and the water or brine inlet means.

6. The apparatus according to claim 1, wherein the tubes are in the form of a coil.

7. The apparatus according to claim 1, wherein the pump, the tubes and the flowmeter are manufactured from materials chosen from the group consisting of:
Austenitic-ferritic steels and
Superalloys containing mainly nickel.

8. The use of the apparatus according to claim 1 in an enhanced oil and/or off-shore gas recovery process.

9. The use of the apparatus according to claim 1 in an enhanced oil and/or on-shore gas recovery process.

10. A method for monitoring the effective dissolving of a water-soluble polymer at a use region thereof where it is not easily accessible, wherein, within a pipe:
a solution is formed, obtained by way of mixing water or brine with an invert emulsion of said polymer, or a powder of said polymer,
the mother solution is diluted,
the diluted solution is transported to the use region thereof,
between the formation of the mother solution and the dilution thereof, part of the stream flowing in the pipe is shunted in order to circulate it within in the apparatus according to claim 1, the viscosity of the diluted solution is calculated by way of the extrapolation of the pressure difference measured by the differential pressure measuring device of the apparatus according to claim 1, a viscosity is measured of a polymer solution prepared at a same concentration as that of the diluted solution, and under optimum laboratory conditions, a ratio is calculated between the value of viscosity obtained by extrapolation and the viscosity of the solution made in the laboratory, satisfactory or unsatisfactory dissolving of the polymer is deduced therefrom.

11. The method according to claim 10, wherein the shear rate in the second calibrated tube is preferentially between 1 $s^{-1}$ and 500 $s^{-1}$.

12. The method according to claim 10, wherein the water-soluble polymer mother solution has a polymer concentration of between 2,000 and 20,000 ppm and the diluted solution has a polymer concentration of between 100 and 2500 ppm.

13. The method according to claim 10, wherein the shear rate in the second calibrated tube is between 5 $s^{-1}$ and 200 $s^{-1}$.

* * * * *